United States Patent [19]

King

[11] 4,443,754
[45] Apr. 17, 1984

[54] METHOD FOR DETERMINING MINIMUM LUBRICATING OIL-FILM THICKNESS UNDER OPERATING ENGINE CONDITIONS USING ELECTRICAL CAPACITANCE

[75] Inventor: William H. King, Florham Park, N.J.

[73] Assignee: Exxon Research and Engineering Co., Florham Park, N.J.

[21] Appl. No.: 434,945

[22] Filed: Oct. 18, 1982

[51] Int. Cl.³ ............................................. G01R 27/26
[52] U.S. Cl. ....................................... 324/61 R; 73/64
[58] Field of Search ........................ 73/9, 593, 10, 64; 324/61 R

[56] References Cited

U.S. PATENT DOCUMENTS 3,182,255 5/1965 Hopkins .............................. 73/64 X
3,227,951 1/1966 Dykaar .............................. 324/61 R
3,331,019 7/1967 Irwin .................................. 324/61 R

OTHER PUBLICATIONS

"Engine Diagnosis Systems Developed by Fiat Research Center", Fiat Research Center Brochure, 1980.
S. L. Moore, "Measurement of the Ring to Linear Oil Film Thickness in Caterpillar 1-G Diesel Engine" in SAE Paper No. 790730, (1979), pp. 1–12.
S. L. Moore, "Piston Ring Lubrication in a Two-Stroke Diesel Engine" in Wear, 72 (1981), pp. 353–369.
K. Ninomiya et al., "Electrical Observation of Lubricant Film Between a Cam and a Lifter of an OHV Engine," SAE Paper No. 780930, (1978), pp. 1–10.

*Primary Examiner*—Stanley T. Krawczewicz
*Assistant Examiner*—Jose M. Solis
*Attorney, Agent, or Firm*—Eugene Zagarella, Jr.

[57] ABSTRACT

This invention relates to a method for determining the minimum oil-film thickness of a lubricating oil composition under engine operating conditions using selected electrical capacitance means wherein a potential relating to the capacitance is developed across an electrically isolated bearing and crankshaft, said capacitance being converted through a derived formula to the minimum oil-film thickness at the particular time the potential is being applied.

9 Claims, 4 Drawing Figures

FIG. I

METHOD FOR DETERMINING MINIMUM LUBRICATING OIL-FILM THICKNESS UNDER OPERATING ENGINE CONDITIONS USING ELECTRICAL CAPACITANCE

BACKGROUND OF THE INVENTION

This invention relates to a method for determining the mininum oil-film thickness of a lubricating oil composition under engine operating conditions using electrical capacitance means.

The hydrodynamic and rheological properties of a lubricant composition and its ability to maintain suitable film thickness for different applications has long been considered by those involved with the theory and application of lubrication technology. While various studies have been made and a number of tests developed for measuring or evaluating film thickness of lubricating compositions with varying degrees of success, most do not satisfactorily address or consider many of the conditions involved in actual use applications, such as fired automotive engines. This can be readily understood, since most test techniques do not involve the squeeze-film conditions experienced in a fired engine. Many of the previous studies of lubricant properties have been based on direct film thickness as used in laboratory bench tests or bearing rigs which do not provide the aforesaid squeeze-film conditions of a fired engine, and indirect measurement in fired engines obtained by monitoring phenomena such as wear, temperature rise, and oil flow.

Several other techniques have been reported for measuring oil-film thickness. Some of these techniques used magnetic sensors or capacitance probes which were placed in, for example, a bearing, and detected the proximity of another surface across the oil film. One such technique is exemplified in SAE Paper 790730 by S. L. Moore entitled "Measurement of the Ring to Linear Oil Film Thickness in a Caterpillar 1-G Diesel Engine," 1979. These techniques generally have the disadvantages of (1) a more complicated change in design to accommodate the probe, (2) interfereing with the normal oil flow in the apparatus and (3) measuring film thickness only at one point, which may not be the point of minimum thickness.

Other studies involving electrical means included that found in SAE Paper 780930 by K. Ninomiya et al entitled "Electrical Observation of Lubricant Film Between a Cam and a Lifter of an OHV Engine," 1978. In this work they were measuring the extent of metallic contact between heavily loaded surfaces. Another technique was disclosed by Fiat involved an engine diagnosis system which used an instrument called a Crankshaft Lubmeter to measure oil-film thickness in bearings by electrical means. In this technique the electrical resistance of the oil-film is measured using somewhat complicated electrical circuitry. The difficulty with measuring the instantaneous electrical resistance of the oil-film is that the surfaces become polarized which increases the apparent resistance of the oil-film and thus leads to error. While this can be avoided by using an AC circuit, it complicates the circuitry even more.

While all of the above methods and apparatus provide some measure for considering lubricant film and the properties thereof under selected conditions, there still remains the need for a simple, relatively direct method in which the film thickness of lubricant compositions can be evaluated when under actual operating conditions.

SUMMARY OF THE INVENTION

Now, in accordance with this invention, a method and apparatus for evaluating the film thickness of lubricating oil compositions when under operating or fired engine conditions has been developed. More particularly, this invention relates to a relatively simple method for determining the minimum oil-film thickness of a lubricating oil composition under engine operating conditions using electrical capacitance means.

The present invention is directed to a method for determining the minimum oil-film thickness of a lubricating oil composition under operating engine conditions comprising:

(a) placing the lubricating oil composition being evaluated in an operating engine wherein a selected bearing of said engine is electrically isolated;

(b) obtaining an instantaneous signal relating to capacitance from between the bearing and shaft and measuring the capacitance using capacitance measuring means, said capacitance measuring means employing a high enough frequency to avoid the ambiguous effect of oil conductivity and a low enough potential to avoid electrical discharge between the surfaces; and (c) converting said capacitance signal developed between said bearing and shaft to a value indicative of the minimum oil-film thickness between said bearing and shaft at the particular time said capacitance signal is obtained.

More particularly, this invention is directed to a simplified method for determining the minimum oil-film thickness of a lubricating oil composition under operating engine conditions comprising:

(a) placing the lubricating oil composition in an operating engine wherein a selected bearing of said engine is electrically isolated, (b) applying an alternating current between the crankshaft and selected bearing of said engine, said current being low enough to prevent electrical discharge between the two surfaces and said alternating current being applied at a frequency which is high enough to avoid the ambiguous effect of oil conductivity, (c) measuring the potential developed between said crankshaft and bearing at any selected time during an engine cycle, said measurement directly relating to the capacitance between said surfaces and (d) converting the capacitance to a value indicative of the minimum oil-film thickness between said crankshaft and bearing at the particular selected time.

BRIEF DESCRIPTION OF THE DRAWINGS

The instant invention may be better understood by reference to the accompanying drawings wherein.

DETAILED DESCRIPTION OF THE INVENTION

Figure 1:
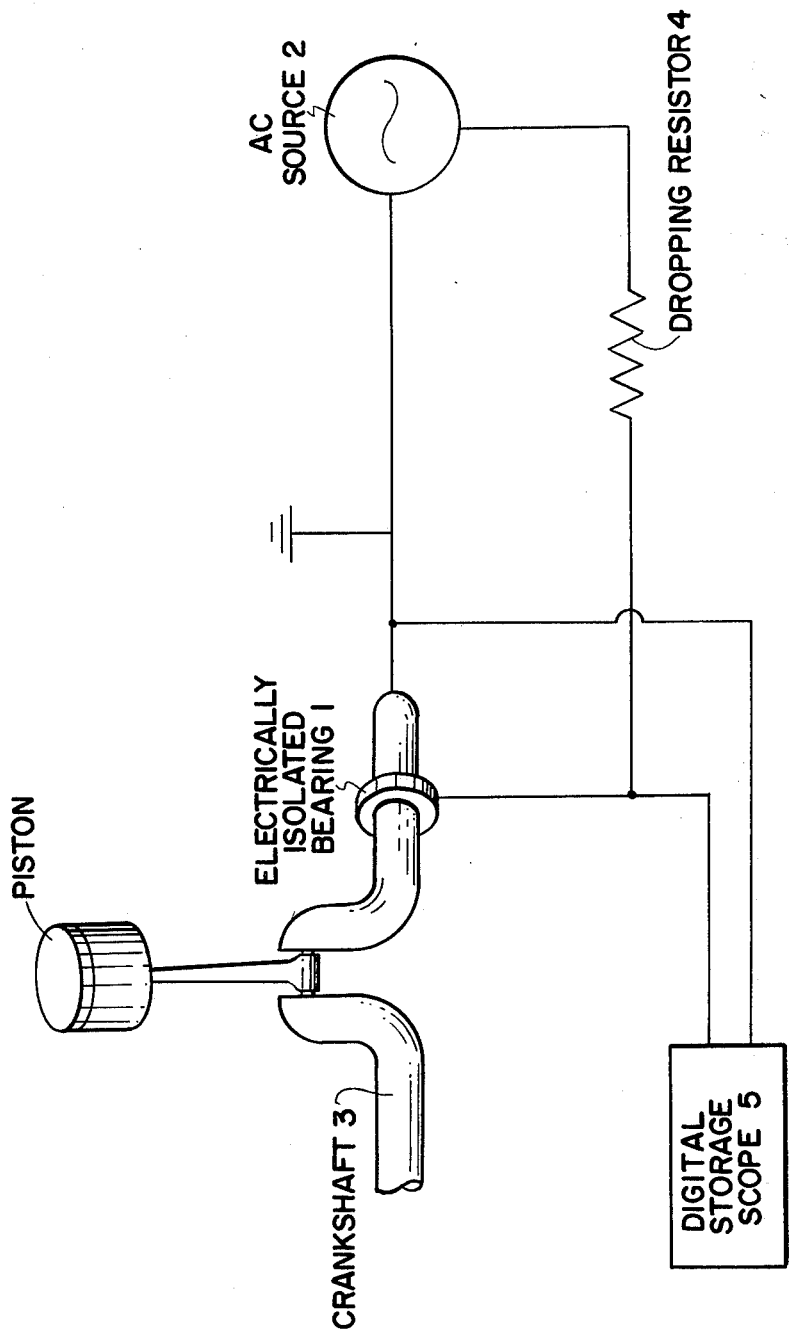
FIG. 1 illustrates schematically the overall arrangement of the apparatus used in carrying out the method of this invention.

As briefly described previously, this invention involves a simple, relatively direct method for determining the minimum oil-film thickness of a lubricating oil under engine operating conditions. Basically, the invention is for a method and apparatus for determining the instantaneous minimum oil-film thickness of a lubricant in a fired engine using electrical copacitance measuring means.

In carrying out the method of this invention, one of the main bearings of an engine, such as a single-cylinder CLR (Cooperative Lubrication Research) engine, is isolated from the engine block and a capacitance signal is developed between the crankshaft and isolated bearing. In this technique, the entire bearing in effect acts as the capacitor or one plate of a capacitor. The resulting potential difference or signal corresponds to or can be directly converted to the capacitance between the bearing and shaft at the particular time of the signal. From this measurement of the instantaneous capacitance between the bearing and shaft, the corresponding instantaneous eccentricity and the minimum film thickness between such surfaces can be determined using formulas which will be described hereinafter.

The capacitance can be obtained using any of several recognized methods of measuring electrical capacitance such as a constant current circuit, a bridge circuit, a timing circuit and a variable frequency oscillation circuit. These and other capacitance measuring techniques are well known in the art as illustrated, for example, in "McGraw-Hill Encyclopedia of Science and Technology," Vol. 2, pp. 473-478, 1971. The important aspect related to the method of this invention is that in determining the capacitance (1) a high enough frequency be used to avoid the ambiguous effect of oil conductivity and also to resolve small differences in engine angle and (2) a low enough potential is used to avoid electrical discharge between the surfaces.

In the preferred embodiment of this invention, a relatively simple method for determining the capacitance between the shaft and bearing is used. This involves the use of a small alternating current (AC) imposed between the crankshaft and isolated bearing. The potential developed between the bearing and shaft is measured and recorded on an oscilloscope. If the current or charge and frequency is kept essentially the same or constant, the resulting potential in volts is inversely related to the capacitance in accordance with the following standard formulas:

$$X_c = \frac{1}{2\pi FC}$$

$$E = IX_c = \frac{I}{2\pi FC}$$

where:
$X_c$ is the capacitive impedance (ohms)
F is the frequency (hertz)
C is the capacitance (farads)
E is the potential (volts)
I is the current (amperes).

Thus, the resulting potential across the bearing and crankshaft gives an output voltage signal on the oscilloscope that is inversely related to the capacitance when the current and frequency are kept essentially constant. In this relationship a low voltage signifies a large capacitance and, conversely, a high voltage signifies a small capacitance. The oscilloscope can be calibrated by referencing against a series of known capacitances and measuring the corresponding voltage values. At any point in the cycle, the output voltage can be measured and converted into a capacitance.

Knowing the capacitance, along with the bearing area, the radial clearance and the dielectric constant of the lubricating oil, the eccentricity ratio and the minimum oil-film thickness can be calculated in accordance with the following formulas:

The capacitance of two parallel plates is defined as:

$$C = \frac{KA\Sigma}{h} \quad (1)$$

where:
A is the area of the plate
$\Sigma$ is the dielectric constant of the material between the plates
h is the distance separating the plates
K is a constant (0.08854).

For an eccentric bearing, the separation of the two surfaces is not constant but varies according to the relationship:

$$h = s(1 - e\cos\theta) \quad (2)$$

where:
s is the radial clearance
e is the eccentricity ratio (0 when centered, 1 when touching)
$\theta$ is the angle around the bearing.

The value of 1/h in equation (1) must then be averaged by integration to give:

$$C = \frac{KA\Sigma}{s\sqrt{1-e^2}} \quad (3)$$

or rearranging $$e = \sqrt{1 - \left(\frac{KA\Sigma}{sC}\right)^2} \quad (4)$$

The minimum oil film thickness (MOFT) at any instant is then:

$$MOFT = s(1-e) = s\left(1 - \sqrt{1 - \left(\frac{KA\Sigma}{sC}\right)^2}\right)$$

These equations contain two implicit assumptions. The first is that the bearing and the journal are both perfectly round. At extremely high eccentricities, some localized deformation of the bearing might be expected. This may lead to an error in the very low MOFT values; however, any such error will be the same for all lubricant oils and therefore will not affect the relative ratings. Second, it is assumed that oil completely fills the annular space between the journal and the bearing, i.e., that cavitation does not occur. If cavitation does occur, the calculated OFT will generally be greater than the actual OFT, i.e., when using an oil which has a dielectric constant of about 2.3 and is thus greater than that of air which is 1.0. If the cavitation occurs opposite to the point of minimum OFT, the error will be small, because this part of the bearing contributes very little to the total capacitance. If the cavitation occurs in the diverging part of the bearing, the error will be larger. Thus, if the entire 180° of the diverging part is cavitating, the calculated film thickness could be about twice that of the actual film thickness.

The apparatus for carrying out the method of this invention is shown schematically in FIG. 1. One of the main bearings 1 of an engine is isolated electrically from the engine block and an alternating current 2 is applied between the crankshaft 3 and isolated bearing 1 across dropping resistor 4. The resulting potential difference between the bearing 1 and crankshaft 3 then passes to a digital storage oscilloscope 5.

Figure 2:
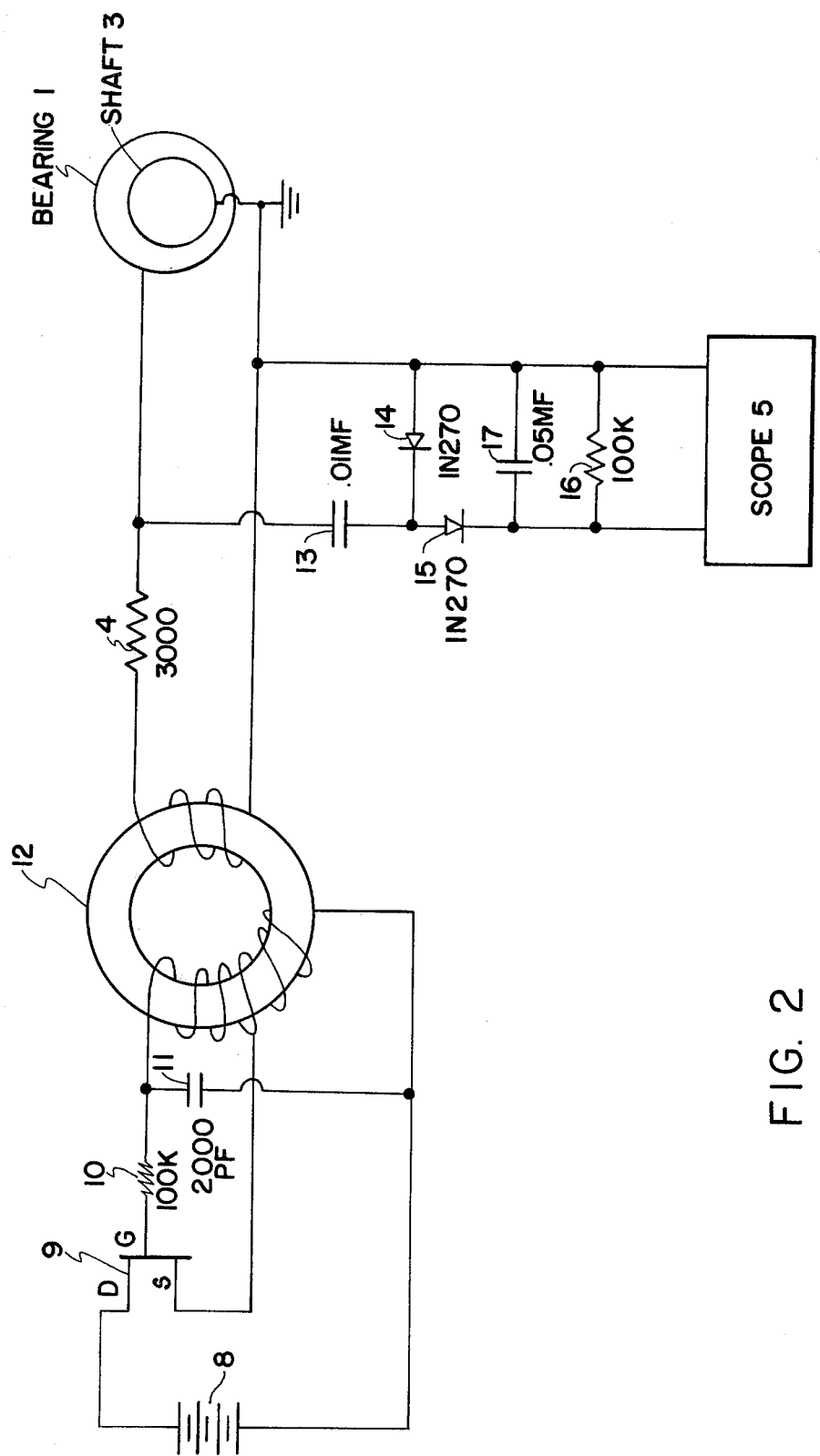
FIG. 2 illustrates a circuit schematic diagram of the apparatus and method of this invention.

FIG. 2 shows the circuit diagram for one preferred embodiment of the system and includes an applied voltage source 8 which is converted to an alternating current using a 100 KHz oscillator. The oscillator is made up of a 15 volt source, 8, a field effect transistor 9 (2N 5958 "N" FET) which includes a 100K ohm resistor 10, and a 2000 PF capacitor 11, as well as a ferrite torroid transformer 12 ($\frac{3}{8}'' \times 3/16''$) with 16 turns of wire to make 0.75 m henri of inductance. The 100 KHz oscillator provides an output of 3 volts RMS and this passes through a dropping resistor 4 and provides an alternating current of about 1 ma. The resulting potential difference between the bearing 1 and crankshaft 3 passes through a rectifier filter circuit which comprises a 0.01 MF capacitor 13, rectifier or diodes 14 and 15, a 100K resistor 16 and a 0.05 MF capacitor 17 to the output or oscilloscope 5.

Figure 3:
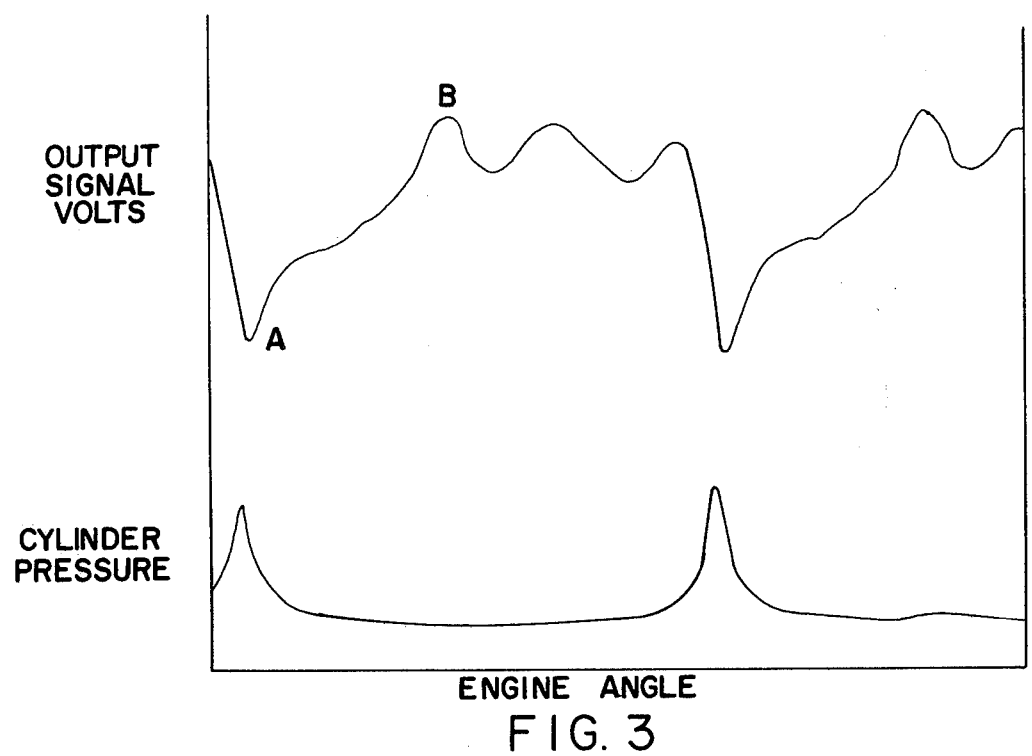
FIGS. 3 and 4 illustrate typical oscilloscope outputs when using the apparatus and method of this invention.

FIG. 3 shows a typical oscilloscope output for one engine cycle with the output signal or voltage as well as the cylinder pressure being shown for the cycle. As noted earlier this voltage or output signal corresponds to the capacitance with a low voltage signifying large capacitance and a high voltage signifying small capacitance. The capacitance figures can be converted into oil-film thickness as discussed above and in this chart, point A represents the point of lowest voltage which signifies the largest capacitance and minimum oil film thickness over the entire cycle. Point B represents the point of highest voltage, lowest capacitance and thickest minimum oil-film.

Figure 4:
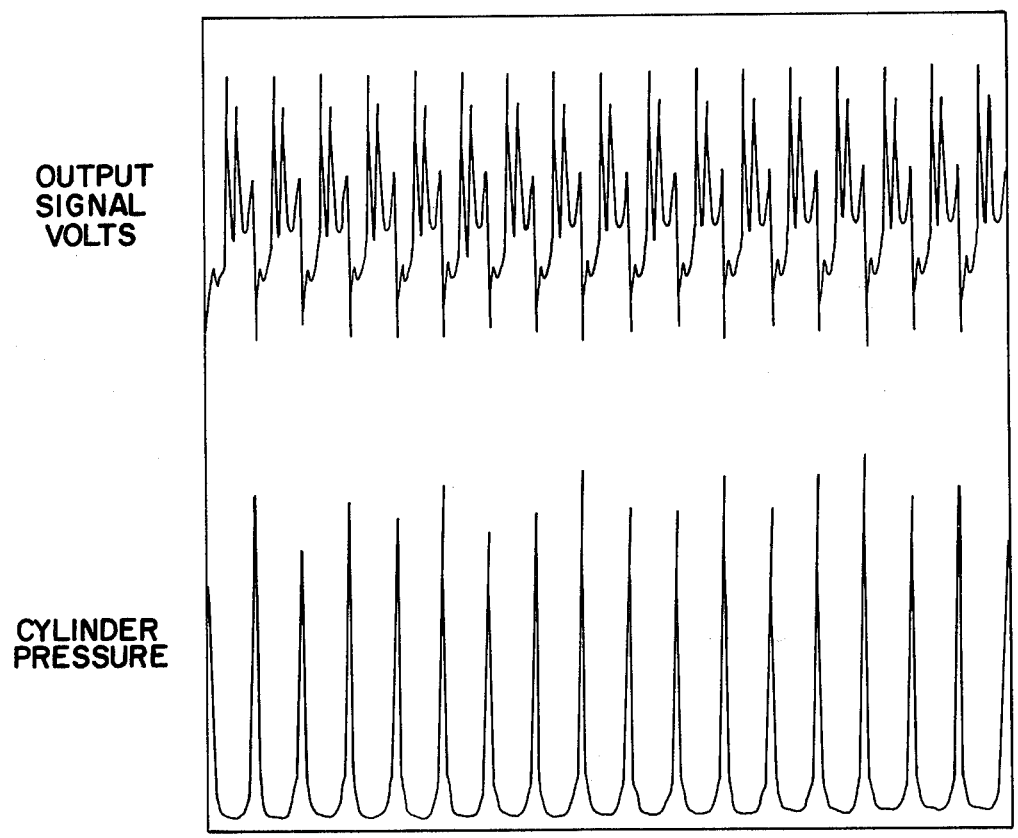

As noted in FIG. 3 and also FIG. 4, the cylinder pressure for the engine cycle or cycles is noted and this is obtained from a pressure transducer attached to the spark plug and the scope and is not shown on the drawings. It is noted in each figure that, generally, the point of minimum output signal or voltage in the cycle which represents the largest capacitance and minimum oil-film thickness, corresponds to the time of maximum cylinder pressure during the cycle.

In carrying out the method of this invention, the applied current and the resulting AC voltage must be low enough to avoid electrical discharge and breakdown. The alternating current should also be applied at a frequency which is high enough to avoid the ambiguous effect of oil conductivity and polarization and to resolve small differences in engine angle. Generally, the current may be up to 4 ma, with a useful range being about 0.01 to about 4 ma, preferably about 0.1 to about 3 ma and more preferably about 0.5 to about 1.5 ma (RMS). Generally, the frequency will vary from about 10 KHz to about 1 MHz and more preferably from about 50 to about 150 KHz. The alternating current as well as the frequency is preferably kept essentially constant, as described above, and this allows the output potential to be converted directly to capacitance. While this is the simplest and preferred method, it is also possible to use other capacitance measuring techniques as described above, however, it would usually require more complicated circuitry to attain the same results.

As indicated above, usually one of the bearings of the engine is electrically isolated. While this is the preferred method, it is also possible to electrically isolate the shaft and while this doesn't give an absolute value for the film thickness, as is the case when the bearing is isolated, it does give a proportional or relative value. Isolating the shaft does have an advantage in that the engine doesn't have to be modified and in this respect is thus even simpler to carry out.

A number of insulating materials may be used in electrically insulating or isolating the bearing from the engine block. Generally, any electrical insulating material which is not permeable to oil may be used with fiberglass plastic laminate being one preferred insulating material.

Any lubricant or lubricating oil composition may be used in the method of this invention, including the mineral lubricating oils and the synthetic lubricating oils and mixtures thereof. Such compositions may, of course, contain any of a number of dispersants, additives and other materials typically found in lubricating oils.

The engine is usually run under operating conditions, i.e., fired or motored, with fired engine operation being particularly preferred.

The following example is further illustrative of this invention and is not intended to be construed as a limitation thereof.

EXAMPLE

A single cylinder CLR engine with one of the main bearings isolated electrically from the engine block was used. The insulation was a fiberglass plastic laminate and was placed on the back of the bearing shell which was shaved 0.005" to allow for its insertion.

As illustrated in FIG. 2, an AC signal source of 100 KH$_z$ and 3 RMS volts was applied through a 3,000 ohm dropping resistor to provide a low constant alternating current of about 1 ma. This current was applied between the isolated main bearing and crankshaft of the aforesaid engine. The resulting potential difference between the bearing and crankshaft then passed through a rectifier and filter capacitor and was fed as the output signal to one channel of an oscilloscope.

The oscilloscope was earlier calibrated by referencing against a series of known capacitances and measuring the corresponding potential or voltage values. Thus, at any point in the cycle, the output signal or voltage which is measured can be directly converted into a capacitance value. This capacitance value can then be converted into a minimum oil-film thickness value using the formulas set forth earlier.

The engine was filled with test oil and the engine allowed to warm up to operating temperature of 100° C. and was then run at a speed of 1,000 rpm and 10 ft.-lbs. FIG. 3 shows a typical oscilloscope output for such run and gives the voltage output which can be directly converted to a capacitance figure since the oscilloscope was previously calibrated. The minimum film thickness for the cycle shown at point A can then be determined by converting the voltage reading to capacitance and then calculating for MOFT which was 1.5 (eccentricity ratio 0.97) $\mu$m for this oil (dielectric constant 2.3) with a radical clearance of 46 $\mu$m. The thickest MOFT for this cycle is found at point B and was 17 μm (eccentricity ratio of 0.63).

Another oscilloscope output for the same oil is shown in FIG. 4. This figure displays a single oscilloscope trace giving a set of 17 engine cycles and shows the excellent repeatability and sensitivity of the method of this invention for determining capacitance and minimum oil-film thickness.

What is claimed is:

1. A method for determining the minimum oil-film thickness of a lubricating oil composition under operating engine conditions comprising:
   (a) placing the lubricating oil composition being evaluated in an operating engine wherein a selected bearing of said engine is electrically isolated;
   (b) obtaining an instantaneous signal relating to capacitance between the entire bearing and shaft and measuring the capacitance using capacitance measuring means, said capacitance measuring means employing a high enough frequency to avoid the ambiguous effect of oil conductivity and a low enough potential to avoid electrical discharge between the surfaces; and
   (c) converting said capacitance signal developed between said bearing and shaft to a value indicative of the minimum oil-film thickness between said bearing and shaft at the particular time said capacitance signal is obtained by using the formula:

$$MOFT = s\left(1 - \sqrt{1 - \left(\frac{KA\epsilon}{sC}\right)^2}\right)$$

where:
is the radial clearance
K is a constant (0.08854)
A is the area of the plate
Σ is the dielectric constant of the material between the plates
C is capacitance.

2. A method for determining the minimum oil-film thickness of a lubricating oil composition under operating engine conditions comprising:
   (a) placing the lubricating oil composition being evaulated in an operating engine wherein a selected bearing of said engine is electrically isolated;
   (b) applying an alternating current between the crankshaft of said engine and said entire bearing, said current being applied at a frequency which is high enough to avoid the ambiguous effect of oil conductivity and said current being low enough to avoid electrical discharge between the two surfaces,
   (c) measuring the potential developed between said shaft and bearing at any selected time during an engine cycle, said measurement directly relating to the capacitance therebetween, and
   (d) converting the capacitance to a value indicative of the minimum oil-film thickness between said shaft and said bearing at the particular selected time by using the formula:

$$MOFT = s\left(1 - \sqrt{1 - \left(\frac{KA\epsilon}{sC}\right)^2}\right)$$

where:
s is the radial clearance
K is a constant (0.08854)
A is the area of the plate
Σ is the dielectric constant of the material between the plates
C is the capacitance.

3. The method of claim 2 wherein said alternating current and said frequency is kept essentially constant.

4. The method of claim 3 wherein said current is from about 0.01 to about 4 ma and is applied at a frequency of about 10 KHz to about 1 MHz.

5. The method of claim 4 wherein said current is from about 0.1 to about 3 ma.

6. The method of claim 3 wherein said current is from about 0.5 to about 1.5 ma and said frequency is from about 50 to about 150 KHz.

7. A method for determining the minimum oil-film thickness of a lubricating oil composition under operating conditions comprising:
   (a) placing the lubricating oil composition being evaluated in an operating engine wherein the crankshaft is electrically isolated;
   (b) obtaining an instantaneous signal relating to capacitance between the shaft and bearings of said engine and measuring the capacitance using capacitance measuring means, said capacitance measuring means employing a high enough frequency to avoid the ambiguous effect of oil conductivity and a low enough potential to avoid electrical discharge between the surfaces; and
   (c) converting said capacitance signal developed between said shaft and bearings and which is indicative of the relative capacitance between said surfaces, to a value indicative of the relative minimum oil-film thickness between said surfaces by using the forula:

$$MOFT = s\left(1 - \sqrt{1 - \left(\frac{KA\epsilon}{sC}\right)^2}\right)$$

where:
s is the radial clearance
K is a constant (0.08854)
A is the area of the plate
Σ is the dielectric constant of the material between the plates
C is capacitance.

8. The method of claim 7 wherein said capacitance measuring means comprises an alternating current of from about 0.1 to about 3 ma and a frequency of about 10 KHz to about 1 MHz.

9. The method of claim 8 wherein said capacitance measuring means comprises an alternating current of from about 0.5 to about 1.5 ma and a frequency of about 50 to about 150 KHz.

* * * * *